United States Patent [19]

Marra et al.

[11] Patent Number: 5,234,912
[45] Date of Patent: Aug. 10, 1993

[54] PHARMACEUTICAL COMPOSITIONS COMPRISING RECOMBINANT BPI PROTEINS AND A LIPID CARRIER AND USES THEREOF

[75] Inventors: Marian N. Marra, San Mateo; Randal W. Scott, Cupertino; James L. Snable, Belmont; Craig G. Wilde, Foster City, all of Calif.

[73] Assignee: INCYTE Pharmaceuticals, Inc., Palo Alto, Calif.

[21] Appl. No.: 766,566

[22] Filed: Sep. 27, 1991

Related U.S. Application Data

[63] Continuation-in-part of Ser. No. 681,551, Apr. 5, 1991, Pat. No. 5,171,739, and a continuation-in-part of Ser. No. 725,656, Jul. 3, 1991, said Ser. No. 725,656, is a continuation-in-part of Ser. No. 681,551, Apr. 5, 1991, Pat. No. 5,171,739, which is a continuation-in-part of Ser. No. 567,016, Aug. 13, 1990, which is a continuation-in-part of Ser. No. 468,696, Jan. 22, 1990, Pat. No. 5,089,274, which is a continuation-in-part of Ser. No. 310,842, Feb. 14, 1989, abandoned.

[30] Foreign Application Priority Data

Oct. 12, 1990 [KR] Rep. of Korea ............... 702247/90

[51] Int. Cl.$^5$ ............... A61K 35/14; A61K 37/02; C07K 3/00; C07K 15/06
[52] U.S. Cl. ............... 514/21; 514/12; 424/450
[58] Field of Search ............... 514/12, 21; 424/85.1, 424/450

[56] References Cited

U.S. PATENT DOCUMENTS 4,863,740 9/1989 Kissel et al. ............... 424/85.1
5,089,274 2/1992 Marra et al. ............... 514/21

Primary Examiner—Jeffrey E. Russel
Assistant Examiner—P. Lynn Touzeau
Attorney, Agent, or Firm—John P. White

[57] ABSTRACT

The present invention provides a composition comprising a BPI Protein and a lipid carrier. Additionally, this invention provides a method for solubilizing a BPI protein which comprises contacting the BPI Protein with a lipid carrier under conditions such that the BPI Protein is solubilized.

6 Claims, No Drawings

PHARMACEUTICAL COMPOSITIONS COMPRISING RECOMBINANT BPI PROTEINS AND A LIPID CARRIER AND USES THEREOF

This application is a continuation-in-part of U.S. Ser. No. 681,551, filed Apr. 5, 1991, now U.S. Pat. No. 5,171,739, and U.S. Ser. No. 725,656, filed Jul. 3, 1991. U.S. Ser. No. 725,656, filed Jul. 3, 1991 is a continuation-in-part of U.S. Ser. No. 681,551, filed Apr. 5, 1991, now U.S. Pat. No. 5,171,739, which is a continuation-in-part of U.S. Serial No. 567,016, filed Aug. 13, 1990, which is a continuation-in-part of U.S. Ser. No. 468,696, filed Jan. 22, 1990, now U.S. Pat. No. 5,089,274, which is a continuation-in-part of U.S. Ser. No. 310,842 filed Feb. 14, 1989, now abandoned, the contents of all of which are hereby incorporated by reference.

BACKGROUND OF THE INVENTION

Gram negative infections are a major cause of morbidity and mortality especially in hospitalized and immunocompromised patients. [Duma, R. J., Am. J. of Med., 78 (Suppl. 6A): 154–164 (1985); and Kreger B. E., D. E. Craven and W. R. McCabe, Am. J. Med., 68: 344–355 (1980)]. Although available antibiotics are generally effective in containing the infection, they do nothing to neutralize the pathophysiological effects associated with lipopolysaccharide (LPS).

LPS is a major component of the outer membrane of gram negative bacteria and is released when the organisms are lysed [Shenep, J. L. and K. A. Morgan, J. Infect. Dis., 150 (3): 380–388 (1984)]. LPS released during antibiotic therapy is a potent stimulator of the inflammatory response. Many detrimental effects of LPS in vivo result from soluble mediators released by inflammatory cells [Morrison D. C. and R. J. Ulevich, Am. J. Pathol., 93 (2): 527–617 (1978)]. LPS induces the release of mediators by host inflammatory cells which may ultimately result in disseminated intravascular coagulation (DIC), adult respiratory distress syndrome (ARDS), cardiac dysfunction, organ failure, liver failure (hepatobiliary dysfunction), brain failure (CNS dysfunction), renal failure, multi-organ failure and shock.

Soluble LPS causes decreased neutrophil chemotaxis, increased adhesiveness, elevated hexose monophosphate shunt activity and $O_2$ radical production, upregulation of surface receptors for complement, and release of granule proteins into the surrounding medium [Morrison and Ulevich (1978)].

Endotoxemia is a condition associated with the presence of endotoxins, i.e. heat stable bacterial toxins, in the blood. Endotoxins elicit an inflammatory response that is beneficial in fighting the infection but can be damaging to the host if uncontrolled. Endotoxemia induces production of endotoxin binding proteins from the liver and causes release of microbicidal proteins from leukocytes. Our studies show that one of these leukocyte proteins, i.e. BPI, previously known only for its bactericidal activity in vitro, inhibits the ability of endotoxin to stimulate neutrophils and monocytes in vitro and reduces death due to endotoxin or bacterial challenge when given in vivo. Monocytes and neutrophilic granulocytes play a key role in host defense against bacterial infections and also participate in the pathology of endotoxemia. These cells ingest and kill microorganisms intracellularly and also respond to endotoxin in vivo and in vitro by releasing soluble proteins with microbicidal, proteolytic, opsonic, pyrogenic, complement activating and tissue damaging effects.

Tumor necrosis factor (TNF), a cytokine released by endotoxin stimulated monocytes mimics some of the toxic effects of endotoxin in vivo. Injecting animals with TNF causes fever, shock and alterations in glucose metabolism. TNF is also a potent stimulator of neutrophils. Other cytokines such as IL-1, IL-6, and IL-8 also mediate some of the pathophysiologic effects of LPS.

Despite improvements in antibiotic therapy, morbidity and mortality associated with endotoxemia remains high. Antibiotics alone are not effective in neutralizing the toxic effects of LPS. Therefore, the need arises for a therapy with direct endotoxin neutralizing activity. Current methods for treatment of endotoxemia use antibiotics and supportive care. Most available adjunct therapies treat symptoms of endotoxic shock such as low blood pressure and fever but do not inactivate endotoxin. Other therapies inhibit inflammatory host responses to LPS. As indicated below, present therapies have major limitations due to toxicity, immunogenicity, or irreproducible efficacy between animal models and human trials.

Polymyxin B (PMB) is a basic polypeptide antibiotic which has been shown to bind to, and structurally disrupt, the most toxic and biologically active component of endotoxin, Lipid A. PMB has been shown to inhibit endotoxin activation of neutrophil granule release in vitro and is a potential treatment for gram negative infections in humans. However, because of its systemic toxicity, this drug has limited use except as a topical agent.

Combination therapy using antibiotics and high doses of methylprednisolone sodium succinate (MPSS) has been shown to prevent death in an experimental model of gram negative sepsis using dogs. Another study using MPSS with antibiotics in a multicenter, double blind, placebo-controlled, clinical study in 223 patients with clinical signs of systemic sepsis concluded that mortality was not significantly different between the treatment and placebo groups. Further, the investigators found that resolution of secondary infection within 14 days was significantly higher in the placebo group.

A relatively new approach to treatment of endotoxemia is passive immunization with endotoxin neutralizing antibodies. Hyperimmune human immunoglobulin against E. coli J5 has been shown to reduce mortality in patients with gram negative bacteremia and shock by 50%. Other groups have shown promising results in animal models using mouse, chimeric, and human monoclonal antibodies. Although monoclonal antibodies have advantages over hyperimmune sera, e.g. more consistent drug potency and decreased transmission of human pathogens, there are still many problems associated with administering immunoglobulin to neutralize LPS. Host responses to the immunoglobulins themselves can result in hypersensitivity. Tissue damage following complement activation and deposition of immune complexes is another concern in the use of therapies involving anti-endotoxin antibodies in septic patients.

BPI is a neutrophil granule protein first discovered in 1975 [Weiss, J., R. C. Franson, S. Becherdite, K. Schmeidler, and P. Elsbach J. Clin. Invest., 55:33 (1975)]. BPI was obtained in highly purified form from human neutrophils in 1978 and was shown to increase membrane permeability and have bactericidal activity against gram negative bacteria when assayed in phosphate buffered saline in vitro [Weiss, J., et al. J. Biol. Chem, 253(8): 2664-2672 (1978)]. Weiss et al. [J. Biol. Chem. 254(21): 11010-11014 (1979)], further showed that BPI increased phospholipase A2 activity suggesting a proinflammatory activity for BPI in addition to its in vitro bactericidal activity.

Rabbit BPI was purified in 1979 [Elsbach et al. J. Biol. Chem 254(21): 11000-11009] and shown to have identical bactericidal and permeability increasing properties as BPI from humans providing a further source of material for study. Both BPI from rabbit and human were shown to be effective against a variety of gram negative bacteria in vitro, including K1-encapsulated *E. coli* [Weiss et al. Infection and Immunity 38(3): 1149-1153, (1982)].

A role for lipopolysaccharide in the in vitro bactericidal action of BPI was proposed in 1984 by Weiss et al. [J. Immunol. 132(6): 3109-3115, (1984)]. These investigators demonstrated that BPI bound to the outer membrane of gram-negative bacteria, caused extracellular release of LPS, and selectively stimulated LPS biosynthesis. In 1984 a protein with similar properties was isolated from human neutrophils and designated cationic antimicrobial protein 57 (CAP 57) [Shafer, W. M., C. E. Martin and J. K. Spitznagel, Infect. Immun., 45:29 (1984)] This protein is identical to BPI as determined by the N-terminal amino acid sequence, amino acid composition, molecular weight and source [Spitznagel et al., Blood 76:825-834, 1990[. Another group, Hovde and Gray, reported a bactericidal glycoprotein with virtually identical properties to BPI in 1986 [Hovde and Gray, Infection and Immunity 54(1): 142-148 (1986)].

In 1985 Ooi et al. reported that BPI retained its in vitro bactericidal activity after cleavage with neutrophil proteases suggesting that fragments of the molecule retain activity [(Ooi and Elsbach, Clinical Research 33(2):567A (1985)]. All of the in vitro bactericidal and permeability increasing activities of BPI were present in the N-terminal 25 kD fragment of the protein [(Ooi, C. E., et al. J. Biol. Chem. 262: 14891 (1987)]

Evidence that BPI binds to a structure associated with endotoxin on the outer membrane of bacteria is as follows: (1) increased sensitivity of rough strains of *E. coli* relative to smooth strains to the permeability increasing activities of BPI [Weiss, J. et al. Infect. Immun. 51:594 (1986)]; (2) the Prm A mutation which results in altered endotoxin structure caused decreased binding of both polymyxin B. and BPI [Farley, M. M. et al. Infect. Immun. 56:1536-1539 (1987) and Farley et al. Infect. Immun. 58:1589-1592 (1988)]; (3) polymyxin B (PMB) completer with BPI for binding to *S. tychimurium* [Farley 1988]; and (4) BPI shared amino acid sequence homology and immunocrossreactivity to another endotoxin binding protein termed Lipopolysaccharide Binding Protein LBP) [Tobias et al., J. Biol. Chem. 263(27): 13479-13481 (1988). LBP-LPS complexes bind to a cell surface receptor on monocytes (CD 14) which results in increased synthesis and release of the inflammatory cytokine tumor necrosis factor (TNF) [Schumann et al. Science 249:1429-1431]. Thus, LBP promotes the immunostimulatory activities of LPS. BPI has exactly the opposite effect of LBP. BPI binds LPS and inhibits neutrophil and monocyte activation [Marra et al., J. Immunol. 144:662-666 (1990); Marra and Scott, W090/09183, published 23 August 1990; C. J. Fisher ®t al. Circulatory Shock 34: 120 (1991)].

A cDNA encoding BPI was obtained and sequenced by Gray et al. [Gray et al. Clin. Res. 36:620A (1988) and Gray et al. J. Biol. Chem. 264(16): 9505-9506 (1989)]. They reported that BPI is a membrane protein which can be cleaved and released in soluble form as a 25 kDa fragment.

BPI binding to gram negative bacteria was reported originally to disrupt LPS structure, alter microbial permeability to small hydrophobic molecules and cause cell death (Weiss, et al., 1978). More recently these same authors have demonstrated that such effects occur only in the absence of serum albumin. BPI has no bactericidal activity when added to bacteria cultured in the presence of serum albumin, thus suggesting that BPI does not kill bacteria in vivo where albumin is ubiquitous [Mannion et al. J. Clin. Invest. 85: 853-860 (1990) and Mannion et al J. clin. Invest. 86: 631-641]. Thus it has been previously understood in the art that the beneficial effects of BPI are limited to in vitro bactericidal effects.

Further, BPI is described by Gray et al. [J. Biol. Chem. 264 (16): 9505-9509 (1989)] as a membrane protein which must be cleaved to the 25 kDa fragment to be released from the neutrophil granule membrane in soluble form. The present invention provides for a method of producing soluble BPI in active form. Further the present invention separates for the first time two molecular forms of the molecule apparently unresolved by Gray et al. representing glycosylated and nonglycosylated forms of the molecule which appear to have different serum half-life profiles in vivo and thus different therapeutic potential. BPI from neutrophils is a mixture of the glycoslyated and nonglycosylated forms.

In contrast to the prior art the present invention demonstrates how to make soluble recombinant BPI and further demonstrates that BPI is a protein that binds endotoxin and inhibits the immunostimulatory and toxic activities of LPS both in vitro and in vivo. Thus, BPI has a novel and distinct use in the therapeutic and prophylactic treatment of endotoxin-related disorders. Furthermore, the present invention provides a composition comprising BPI and a lipid carrier, which composition retains inhibitory activity against endotoxin and is more stable to physical agitation and manipulations. Such a composition represents a substantial improvement over the state of the art in maintaining BPI soluble, active form.

SUMMARY OF THE INVENTION

The present invention provides a composition comprising a BPI Protein and a lipid carrier. The subject invention is useful for both therapeutic and diagnostic modalities. For therapeutic modalities, a pharmaceutically acceptable lipid carrier is preferred.

Additionally, this invention provides a method for solubilizing a BPI Protein which comprises contacting the BPI Protein with a lipid carrier under conditions such that the BPI Protein is solubilized.

DETAILED DESCRIPTION OF THE INVENTION

As used in this application, the following words or phrases have the meanings specified.

As used herein, "BPI" means a native or naturally occurring biologically active human 57kd protein which binds to the outer membrane of susceptible gram negative bacteria.

As used herein, "biologically active polypeptide fragment of BPI" means a polypeptide of molecular weight less than 57 kd, having the biological activity of, and an amino acid sequence present within, BPI.

As used herein, "biologically active polypeptide analogs of BPI" means a polypeptide which has substantially the same amino acid sequence as, and the biological activity of, BPI. Biologically active polypeptide analogs of BPI include polypeptide, the sequence of which varies from the sequence of BPI by a changed amino acid within the BPI sequence, e.g. a mutation, or by the addition of one or more amino acids at the amino- or carboxy-terminus, or both, of the BPI sequence.

As used herein, "biologically active variant of BPI" means a polypeptide that (1) includes a portion of the amino acid sequence which is present within BPI and an amino acid sequence which is not present within BPI, and (2) has substantially the same biological activity, i.e. endotoxin-neutralizing activity, as BPI.

As used herein, "recombinant" means a polypeptide produced by genetic engineering methods. Thus, each of BPI, biologically active polypeptide fragments of BPI, biologically active polypeptide analogs of BPI, and biologically active variants of BPI may be recombinant. However, in the context of this application, BPI is not the same as recombinant BPI, the latter differing in some molecular characteristic from the native or naturally occurring polypeptide, e.g. in glycosylation pattern.

As used herein, BPI Protein means (1) BPI, (2) a biologically active fragment of BPI, (3) a biologically active polypeptide analog of BPI, or (4) a biologically active variant of BPI, each of which may be either recombinant or nonrecombinant.

The present invention provides a composition comprising a BPI Protein and a lipid carrier. A pharmaceutically acceptable lipid carrier is preferred for used in medicinal products designed for internal use.

As used in this application a lipid carrier is any fat soluble substance which inhibits protein precipitation. Lipid carriers may comprise sterile solutions, and gels. Compositions comprising such lipid carriers are formulated by well known conventional methods.

In accordance with the practice of the invention, a lipid carrier may be Lipid A or an analog thereof. A Lipid A analog is any substance which is capable of competing with lipid A for binding to a BPI Protein.

Alternatively, the lipid carrier may be a phospholipid. Further, the lipid carrier may be a fatty acid. Also, the lipid carrier may be a detergent. As used herein, a detergent is any substance that alters the surface tension of a liquid, generally lowering it. In one example of the invention, the detergent may be a nonionic detergent. Examples of nonionic detergents include, but are not limited to, polysorbate 80 (also known as TWEEN (polyoxyethylene derivatives of fatty acid partial esters of sorbitol anhydrides) 80 or (polyoxyethylenesorbitan monooleate), Brij, polysorbate 80, and TRITON (surfactant based on alkylaryl polyether alcohols, sulfonates and sulfates) (for example TRITON WR-1339 and TRITON A-20).

Alternatively, the detergent may be an ionic detergent. An example of an ionic detergent includes, but is not limited to, alkyltrimethylammonium bromide.

Additionally, in accordance with the invention, the lipid carrier may be a liposome. As used in this application, a "liposome" is any membrane bound vesicle which contains a desired substance, such as BPI, biologically active polypeptide fragment of BPI, biologically active polypeptide analog of BPI, biologically active polypeptide variant of BPI or any combination thereof.

It should also be apparent to those skilled in the art that other endotoxin binding proteins homologous to BPI may also be stabilized using said lipid carriers. More specifically, lipopolysaccharide binding protein (LBP) may be formulated with a lipid carrier.

Additionally, this invention provides a method for solubilizing a BPI Protein which comprises contacting the BPI Protein with a lipid carrier under conditions such that the BPI Protein is solubilized. This method could be used for solubilizing and refolding of recombinant BPI Protein made in bacteria.

This invention is illustrated in the Experimental Details section which follows. This section is set forth to aid an understanding of the invention but is not intended to, and should not be construed to, limit in any way the invention as set forth in the claims which follow.

Experimental Details

EXAMPLE 1

Precipitation of recombinant BPI (rBPI) by mechanical agitation. Sample of rBPI in 50 mM Tris, 1M NaCl, pH 7.4 contained in half-full test tubes (generating a significant air-liquid interface) will precipitate within 30 minutes if agitated on a rocker platform (Labquake Shaker, Cat. No. 400-110 Lab Industries, Berkeley, Calif.). Similar efficiency of precipitation is observed upon vortexing of rBPI solution for 5 minutes. Typically, yields for either method of precipitation are approximately 97% precipitated.

The effect of different agents on rBPI solubility. Recombinant BPI (1.6 milligrams per milliliter) in 50mM Tris 1M NaCl pH 7.4 was diluted 10 fold into the following solutions and agitated overnight at 4° C. using a rocker platform. Each solution was then observed for visible precipitation (Table I).

TABLE I

| Solution present(visual) | precipitate |
| --- | --- |
| 50 mM Tris pH 7.4 100 mM NaCl | X |
| 50 mM Tris pH 7.4 1M NaCl | X |
| 50 mM Tris pH 7.4 10 mM DTT | X |
| 50 mM Tris pH 7.4 10 mM Ascorbic Acid | X |
| 50 mM Tris pH 7.4 (under Argon) | X |
| 40 mM Citrate pH 4 | X |
| 40 mM Citrate pH 5 | X |
| 40 mM Citrate pH 6 | X |
| 40 mM Citrate pH 7 | X |
| 50 mM Glycine pH 3 | — |
| 0111.B4 LPS 200 µg/ml (pre-incubated 30' @ 38° | — |
| Bovine Serum Albumin 100 µg/ml | X |
| Bovine Serum Albumin 1 mg/ml | X |
| 100 mM Arginine pH 8 | X |
| 1M Arginine pH 8 | X |
| 0.05% TRITON X-114 | — |

X = precipitate observed
— = no precipitate observed

EXAMPLE 2

Effect of Various Lipid or Detergent Carriers on BPI Solubility. The following reagents were added to rBPI (0.16 mg/ml final concentration) and the solution was agitated on a rocker platform for 30 minutes. Solubility was determined by absorbance at 280 nm before and after agitation (Table 2).

TABLE 2

| Condition | % soluble |
| --- | --- |
| 0.5 mM TRITON X-114 | 90 |
| 0.1 mM TRITON X-114 | 59 |
| 0.003% TWEEN 80* | 3 |
| 0.0007% TWEEN 80 | 3 |
| 50 mM Octyl Glucoside | 2 |
| 25 mM Octyl Glucoside | 29 |
| 12.5 mM Octyl Glucoside | 81 |
| 6.25 mM Octyl Glucoside | 60 |
| 3.12 mM Octyl Glucoside | 83 |
| 1.56 mM Octyl Glucoside | 64 |
| 5% polyethylene glycol 6000 | 10 |
| 1% polyethylene glycol 6000 | 2 |
| 0.2% polyethylene glycol 6000 | 2 |
| 20% ethylene glycol | 9 |
| 100 mM ammonium sulfate | 3 |
| 20% glycerol | 9 |
| 0.2% Brij 35* | 101 |
| 0.005% Brij 35 | 97 |
| 0.05% mixed alkyltrimethylammonium bromides | 105 |
| 1M Glucose | 0 |
| 1M Mannose | 0 |
| 1M Galactose | 5 |

*TWEEN 80 = polyoxyethylenesorbitan monooleate
Brij 35 = Polyethylene glycol alkyl ether

EXAMPLE 3

Effect of Tween 80 (polyoxyethylenesorbitan monooleate) on BPI solubility. Additional stability studies using the following concentrations of Tween 80 were performed as described in Example 2 (Table 3). Quantitation was by enzyme linked immunosorbent assay.

TABLE 3

| Condition | % soluble |
| --- | --- |
| 1.0% TWEEN 80 | 187 |
| 0.5% TWEEN 80 | 137 |
| 0.25% TWEEN 80 | 81 |
| 0.125% TWEEN 80 | 30 |

TABLE 3-continued

| Condition | % soluble |
| --- | --- |
| 0.063% TWEEN 80 | 8 |
| 0.0031% TWEEN 80 | 1 |

EXAMPLE 4

BPI in a lipid carrier, i.e. TWEEN 80, effectively protects mice from endotoxin lethality (Table 4).

TABLE 4

Protection from endotoxin lethality by BPI in CD-1 Mice
(LPS-0111:B4 at 25 mg/kg IV)
(SURVIVORS/TOTAL AT 24 HOURS)

| DOSE OF BPI (IV) | BPI IN FORMULATION #1 |
| --- | --- |
| Saline control | 0/5 |
| 5 mg/kg | 5/5 |
| 10 mg/kg | 5/5 |

FORMULATION #1: 20 mM Citrate, 150 mM NaCl, 0.2% TWEEN 80, pH 6.0.

What is claimed is:

1. A composition comprising a BPI Protein and a lipid carrier selected from the group consisting of a phospholipid, a nonionic detergent and a liposome, wherein the BPI Protein is solubilized in the lipid carrier.

2. A composition of claim 1, wherein the lipid carrier is a phospholipid.

3. A composition of claim 1, wherein the lipid carrier is a nonionic detergent.

4. A composition of claim 3, wherein the nonionic detergent is polysorbate 80.

5. A composition of claim 1, wherein the lipid carrier is a liposome.

6. A method for solubilizing a BPI Protein which comprises contacting the BPI Protein with a lipid carrier selected from the group consisting of a phospholipid, a nonionic detergent and a liposome, under conditions such that the BPI Protein is solubilized.

* * * * *

Adverse Decisions In Interference

Patent No. 5,234,912, Marian N. Marra, Randal W. Scott, James L. Snable, Craig G. Wilde, PHARMACEUTICAL COMPOSITIONS COMPRISING RECOMBINANT BPI PROTEINS AND A LIPID CARRIER AND USES THEREOF, Interference No. 103,791, final judgment adverse to the patentees rendered August 27, 1998, as to clsims 1-6.

*(Official Gazette October 27, 1998)*